(12) United States Patent
Nahas

(10) Patent No.: US 8,114,176 B2
(45) Date of Patent: Feb. 14, 2012

(54) CATALYTIC STEAM GASIFICATION OF PETROLEUM COKE TO METHANE

(75) Inventor: Nicholas Charles Nahas, Chatham, NJ (US)

(73) Assignee: Great Point Energy, Inc., Cambridge, MA (US)

( * ) Notice: Subject to any disclaimer, the term of this patent is extended or adjusted under 35 U.S.C. 154(b) by 1958 days.

(21) Appl. No.: 11/249,814

(22) Filed: Oct. 12, 2005

(65) Prior Publication Data

US 2007/0083072 A1    Apr. 12, 2007

(51) Int. Cl.
*C01B 3/32* (2006.01)
*C01B 3/36* (2006.01)
*C01B 6/24* (2006.01)
*B01J 7/00* (2006.01)
*H01M 8/06* (2006.01)
*C10J 3/46* (2006.01)

(52) U.S. Cl. .......... 48/127.3; 48/61; 48/197 R; 423/644
(58) Field of Classification Search .......... 48/61, 197 R, 48/127.3; 423/644
See application file for complete search history.

(56) References Cited

U.S. PATENT DOCUMENTS

| | | | |
|---|---|---|---|
| 2,813,126 A | 11/1957 | Tierney | |
| 2,886,405 A | 5/1959 | Benson et al. | |
| 3,114,930 A | 12/1963 | Oldham et al. | |
| 3,435,590 A | 4/1969 | Smith | |
| 3,531,917 A | 10/1970 | Grunewald et al. | |
| 3,594,985 A | 7/1971 | Ameen et al. | |
| 3,615,300 A | 10/1971 | Holm et al. | |
| 3,689,240 A | 9/1972 | Aldridge et al. | |
| 3,740,193 A | 6/1973 | Aldridge et al. | |
| 3,759,036 A | 9/1973 | White | |
| 3,779,725 A | 12/1973 | Hegarty et al. | |
| 3,828,474 A | 8/1974 | Quartulli | |
| 3,847,567 A | 11/1974 | Kalina et al. | |
| 3,904,386 A | 9/1975 | Graboski et al. | |
| 3,915,670 A | 10/1975 | Lacey et al. | |
| 3,920,229 A | 11/1975 | Piggott | |
| 3,929,431 A | 12/1975 | Koh et al. | |
| 3,958,957 A | 5/1976 | Koh et al. | |
| 3,969,089 A | 7/1976 | Moss et al. | |
| 3,975,168 A | 8/1976 | Gorbaty | |
| 3,985,519 A | 10/1976 | Kalina et al. | |

(Continued)

FOREIGN PATENT DOCUMENTS

CA    966660    4/1975

(Continued)

OTHER PUBLICATIONS

"Integrated Gasification Combined Cycle (IGCC)", WorleyParsons Resources & Energy, http://www.worleyparsons.com/v5/page.aspx?id+164.

(Continued)

*Primary Examiner* — Matthew Merkling
(74) *Attorney, Agent, or Firm* — McDonnell Boehnen Hulbert & Berghoff LLP

(57) ABSTRACT

The present invention provides a catalytic steam gasification process for gasifying petroleum coke. The solids composition within the gasification reactor of the disclosed invention is maintained by controlling the catalyst composition of the feed. The process utilizes sour water from the raw gasification product gases to recover and recycle catalyst. Fine particles generated in the handling of coke are advantageously utilized to increase the efficiency of the process.

20 Claims, 4 Drawing Sheets

U.S. PATENT DOCUMENTS

| | | | |
|---|---|---|---|
| 3,998,607 | A | 12/1976 | Wesselhoft et al. |
| 3,999,607 | A | 12/1976 | Pennington et al. |
| 4,005,996 | A | 2/1977 | Hausberger et al. |
| 4,021,370 | A | 5/1977 | Harris et al. |
| 4,046,523 | A | 9/1977 | Kalina et al. |
| 4,053,554 | A | 10/1977 | Reed et al. |
| 4,057,512 | A | 11/1977 | Vadovic et al. |
| 4,069,304 | A | 1/1978 | Starkovich et al. |
| 4,077,778 | A | 3/1978 | Nahas et al. |
| 4,091,073 | A | 5/1978 | Winkler |
| 4,092,125 | A | 5/1978 | Stambaugh et al. |
| 4,094,650 | A | 6/1978 | Koh et al. |
| 4,100,256 | A | 7/1978 | Bozzelli et al. |
| 4,101,449 | A | 7/1978 | Noda et al. |
| 4,104,201 | A | 8/1978 | Banks et al. |
| 4,118,204 | A | 10/1978 | Eakman et al. |
| 4,152,119 | A | 5/1979 | Schulz |
| 4,157,246 | A | 6/1979 | Eakman et al. |
| 4,159,195 | A | 6/1979 | Clavenna |
| 4,193,771 | A | 3/1980 | Sharp et al. |
| 4,193,772 | A | 3/1980 | Sharp |
| 4,200,439 | A | 4/1980 | Lang |
| 4,204,843 | A | 5/1980 | Neavel |
| 4,211,538 | A | 7/1980 | Eakman et al. |
| 4,211,669 | A | 7/1980 | Eakman et al. |
| 4,219,338 | A | 8/1980 | Wolfs et al. |
| 4,235,044 | A | 11/1980 | Cheung |
| 4,243,639 | A | 1/1981 | Haas et al. |
| 4,260,421 | A | 4/1981 | Brown et al. |
| 4,265,868 | A | 5/1981 | Kamody |
| 4,284,416 | A | 8/1981 | Nahas |
| 4,292,048 | A | 9/1981 | Wesselhoft et al. |
| 4,315,758 | A | 2/1982 | Patel et al. |
| 4,318,712 | A | 3/1982 | Lang et al. |
| 4,330,305 | A | 5/1982 | Kuessner et al. |
| 4,331,451 | A | 5/1982 | Isogaya et al. |
| 4,334,893 | A | 6/1982 | Lang |
| 4,336,034 | A | 6/1982 | Lang et al. |
| 4,336,233 | A | 6/1982 | Appl et al. |
| 4,347,063 | A | 8/1982 | Sherwood et al. |
| 4,348,486 | A | 9/1982 | Calvin et al. |
| 4,348,487 | A | 9/1982 | Calvin et al. |
| 4,353,713 | A | 10/1982 | Cheng |
| 4,365,975 | A | 12/1982 | Williams et al. |
| 4,375,362 | A | 3/1983 | Moss |
| 4,397,656 | A | 8/1983 | Ketkar |
| 4,400,182 | A | 8/1983 | Davies et al. |
| 4,407,206 | A | 10/1983 | Bartok et al. |
| 4,432,773 | A | 2/1984 | Euker, Jr. et al. |
| 4,433,065 | A | 2/1984 | Van Der Burgt et al. |
| 4,436,531 | A | 3/1984 | Estabrook et al. |
| 4,439,210 | A | 3/1984 | Lancet |
| 4,444,568 | A | 4/1984 | Beisswenger et al. |
| 4,459,138 | A | 7/1984 | Soung |
| 4,462,814 | A | 7/1984 | Holmes et al. |
| 4,466,828 | A * | 8/1984 | Tamai et al. ............ 75/430 |
| 4,468,231 | A | 8/1984 | Bartok et al. |
| 4,500,323 | A | 2/1985 | Siegfried et al. |
| 4,508,544 | A | 4/1985 | Moss |
| 4,515,604 | A | 5/1985 | Eisenlohr et al. |
| 4,515,764 | A | 5/1985 | Diaz |
| 4,540,681 | A | 9/1985 | Kustes et al. |
| 4,541,841 | A | 9/1985 | Reinhardt |
| 4,551,155 | A | 11/1985 | Wood et al. |
| 4,558,027 | A | 12/1985 | McKee et al. |
| 4,597,775 | A | 7/1986 | Billimoria et al. |
| 4,597,776 | A | 7/1986 | Ullman et al. |
| 4,604,105 | A | 8/1986 | Aquino et al. |
| 4,609,456 | A | 9/1986 | Deschamps et al. |
| 4,617,027 | A | 10/1986 | Lang |
| 4,619,864 | A | 10/1986 | Hendrix et al. |
| 4,661,237 | A | 4/1987 | Kimura et al. |
| 4,668,428 | A | 5/1987 | Najjar |
| 4,668,429 | A | 5/1987 | Najjar |
| 4,675,035 | A | 6/1987 | Apffel |
| 4,678,480 | A | 7/1987 | Heinrich et al. |
| 4,682,986 | A | 7/1987 | Lee et al. |
| 4,690,814 | A | 9/1987 | Velenyi et al. |
| 4,704,136 | A | 11/1987 | Weston et al. |
| 4,720,289 | A | 1/1988 | Vaugh et al. |
| 4,747,938 | A | 5/1988 | Khan |
| 4,781,731 | A * | 11/1988 | Schlinger ............ 48/197 R |
| 4,803,061 | A | 2/1989 | Najjar et al. |
| 4,822,935 | A | 4/1989 | Scott |
| 4,848,983 | A | 7/1989 | Tomita et al. |
| 4,854,944 | A | 8/1989 | Strong |
| 4,861,360 | A | 8/1989 | Apffel |
| 4,876,080 | A | 10/1989 | Paulson |
| 4,960,450 | A * | 10/1990 | Schwarz et al. ............ 62/642 |
| 4,995,193 | A | 2/1991 | Soga et al. |
| 5,017,282 | A | 5/1991 | Delbianco et al. |
| 5,055,181 | A | 10/1991 | Maa et al. |
| 5,057,294 | A | 10/1991 | Sheth et al. |
| 5,059,406 | A | 10/1991 | Sheth et al. |
| 5,093,094 | A | 3/1992 | Van Kleeck et al. |
| 5,094,737 | A | 3/1992 | Bearden, Jr. et al. |
| 5,132,007 | A | 7/1992 | Meyer et al. |
| 5,223,173 | A | 6/1993 | Jeffrey |
| 5,250,083 | A | 10/1993 | Wolfenbarger et al. |
| 5,277,884 | A | 1/1994 | Shinnar et al. |
| 5,435,940 | A | 7/1995 | Doering et al. |
| 5,536,893 | A | 7/1996 | Gudmundsson |
| 5,616,154 | A | 4/1997 | Elliott et al. |
| 5,630,854 | A | 5/1997 | Sealock, Jr. et al. |
| 5,641,327 | A | 6/1997 | Leas |
| 5,720,785 | A | 2/1998 | Baker |
| 5,733,515 | A | 3/1998 | Doughty et al. |
| 5,776,212 | A | 7/1998 | Leas |
| 5,855,631 | A | 1/1999 | Leas |
| 5,865,898 | A | 2/1999 | Holtzapple et al. |
| 6,013,158 | A | 1/2000 | Wootten |
| 6,015,104 | A | 1/2000 | Rich, Jr. |
| 6,028,234 | A | 2/2000 | Heinemann et al. |
| 6,090,356 | A | 7/2000 | Jahnke et al. |
| 6,180,843 | B1 | 1/2001 | Heinemann et al. |
| 6,187,465 | B1 | 2/2001 | Galloway |
| 6,389,820 | B1 | 5/2002 | Rogers et al. |
| 6,506,349 | B1 | 1/2003 | Khanmamedov |
| 6,506,361 | B1 | 1/2003 | Machado et al. |
| 6,602,326 | B2 | 8/2003 | Lee et al. |
| 6,641,625 | B1 | 11/2003 | Clawson et al. |
| 6,653,516 | B1 | 11/2003 | Yoshikawa et al. |
| 6,692,711 | B1 | 2/2004 | Alexion et al. |
| 6,790,430 | B1 | 9/2004 | Lackner et al. |
| 6,797,253 | B2 | 9/2004 | Lyon |
| 6,808,543 | B2 | 10/2004 | Paisley |
| 6,855,852 | B1 | 2/2005 | Jackson et al. |
| 6,894,183 | B2 | 5/2005 | Choudhary et al. |
| 6,955,695 | B2 | 10/2005 | Nahas |
| 7,074,373 | B1 | 7/2006 | Warren et al. |
| 7,132,183 | B2 | 11/2006 | Galloway |
| 7,220,502 | B2 | 5/2007 | Galloway |
| 7,309,383 | B2 | 12/2007 | Beech, Jr. et al. |
| 2003/0167691 | A1* | 9/2003 | Nahas ............ 48/127.3 |
| 2004/0020123 | A1 | 2/2004 | Kimura et al. |
| 2004/0180971 | A1 | 9/2004 | Inoue et al. |
| 2005/0107648 | A1 | 5/2005 | Kimura et al. |
| 2005/0137442 | A1 | 6/2005 | Gajda et al. |
| 2006/0265953 | A1 | 11/2006 | Hobbs |
| 2007/0000177 | A1 | 1/2007 | Hippo et al. |
| 2007/0051043 | A1 | 3/2007 | Schingnitz |
| 2007/0083072 | A1 | 4/2007 | Nahas |
| 2007/0180990 | A1 | 8/2007 | Downs et al. |
| 2007/0186472 | A1 | 8/2007 | Rabovitser et al. |
| 2007/0277437 | A1 | 12/2007 | Sheth |
| 2009/0048476 | A1 | 2/2009 | Rappas et al. |
| 2009/0090055 | A1 | 4/2009 | Ohtsuka |
| 2009/0090056 | A1 | 4/2009 | Ohtsuka |
| 2009/0165361 | A1 | 7/2009 | Rappas et al. |
| 2009/0165376 | A1 | 7/2009 | Lau et al. |
| 2009/0165379 | A1 | 7/2009 | Rappas |
| 2009/0165380 | A1 | 7/2009 | Lau et al. |
| 2009/0165381 | A1 | 7/2009 | Robinson |
| 2009/0165382 | A1 | 7/2009 | Rappas et al. |
| 2009/0165383 | A1 | 7/2009 | Rappas et al. |
| 2009/0165384 | A1 | 7/2009 | Lau et al. |
| 2009/0166588 | A1 | 7/2009 | Spitz et al. |

| | | | |
|---|---|---|---|
| 2009/0169448 A1 | 7/2009 | Rappas et al. |
| 2009/0169449 A1 | 7/2009 | Rappas et al. |
| 2009/0170968 A1 | 7/2009 | Nahas et al. |
| 2009/0217575 A1 | 9/2009 | Raman et al. |
| 2009/0217582 A1 | 9/2009 | May et al. |
| 2009/0217584 A1 | 9/2009 | Raman et al. |
| 2009/0217585 A1 | 9/2009 | Raman et al. |
| 2009/0217586 A1 | 9/2009 | Rappas et al. |
| 2009/0217587 A1 | 9/2009 | Raman et al. |
| 2009/0217588 A1 | 9/2009 | Hippo et al. |
| 2009/0217589 A1 | 9/2009 | Robinson |
| 2009/0217590 A1 | 9/2009 | Rappas et al. |
| 2009/0218424 A1 | 9/2009 | Hauserman |
| 2009/0220406 A1 | 9/2009 | Rahman |
| 2009/0229182 A1 | 9/2009 | Raman et al. |
| 2009/0246120 A1 | 10/2009 | Raman et al. |
| 2009/0259080 A1 | 10/2009 | Raman et al. |
| 2009/0260287 A1 | 10/2009 | Lau |
| 2009/0324458 A1 | 12/2009 | Robinson et al. |
| 2009/0324459 A1 | 12/2009 | Robinson et al. |
| 2009/0324460 A1 | 12/2009 | Robinson et al. |
| 2009/0324461 A1 | 12/2009 | Robinson et al. |
| 2009/0324462 A1 | 12/2009 | Robinson et al. |
| 2010/0071262 A1 | 3/2010 | Robinson et al. |
| 2010/0076235 A1 | 3/2010 | Reiling et al. |
| 2010/0120926 A1 | 5/2010 | Robinson et al. |
| 2010/0121125 A1 | 5/2010 | Hippo et al. |
| 2010/0168494 A1 | 7/2010 | Rappas et al. |
| 2010/0168495 A1 | 7/2010 | Rappas et al. |
| 2010/0179232 A1 | 7/2010 | Robinson et al. |

FOREIGN PATENT DOCUMENTS

| | | |
|---|---|---|
| CA | 1003217 | 1/1977 |
| CA | 1106178 | 8/1981 |
| CA | 1187702 | 6/1985 |
| CN | 1477090 | 2/2004 |
| DE | 2210891 | 9/1972 |
| DE | 2852710 | 6/1980 |
| DE | 3422202 | 12/1985 |
| DE | 100610607 | 6/2002 |
| EA | 819 | 4/2000 |
| EP | 0 067 580 | 12/1982 |
| EP | 102828 | 3/1984 |
| EP | 0 138 463 | 4/1985 |
| EP | 0 225 146 | 6/1987 |
| EP | 0 259 927 | 3/1988 |
| EP | 0 723 930 | 7/1996 |
| EP | 1 001 002 | 5/2000 |
| EP | 1 741 673 | 6/2006 |
| FR | 797 089 | 4/1936 |
| GB | 593910 | 10/1947 |
| GB | 640907 | 8/1950 |
| GB | 676615 | 7/1952 |
| GB | 701 131 | 12/1953 |
| GB | 760627 | 11/1956 |
| GB | 798741 | 7/1958 |
| GB | 996327 | 6/1965 |
| GB | 1033764 | 6/1966 |
| GB | 1448562 | 9/1976 |
| GB | 1453081 | 10/1976 |
| GB | 1467219 | 3/1977 |
| GB | 1467995 | 3/1977 |
| GB | 1 599 932 | 7/1977 |
| GB | 2078251 | 1/1982 |
| GB | 2154600 | 9/1985 |
| JP | 54020003 | 2/1979 |
| JP | 56157493 | 12/1981 |
| JP | 62241991 | 10/1987 |
| JP | 62 257985 | 11/1987 |
| JP | 2000290659 | 10/2000 |
| JP | 2000290670 | 10/2000 |
| JP | 2002105467 | 4/2002 |
| JP | 2004292200 | 10/2004 |
| JP | 2004298818 | 10/2004 |
| WO | WO 00/43468 | 7/2000 |
| WO | WO 02/40768 | 5/2002 |
| WO | WO 02/079355 | 10/2002 |
| WO | WO 03/033624 | 4/2003 |
| WO | WO 2004/072210 | 8/2004 |
| WO | WO 2006/031011 | 3/2006 |
| WO | WO 2007/005284 | 1/2007 |
| WO | WO 2007/047210 | 4/2007 |
| WO | WO 2007/076363 | 7/2007 |
| WO | WO 2007/128370 | 11/2007 |
| WO | WO 2007/143376 | 12/2007 |
| WO | WO 2008/073889 | 6/2008 |
| WO | WO 2009/018053 | 2/2009 |
| WO | WO 2009/048723 | 4/2009 |
| WO | WO 2009/048724 | 4/2009 |
| WO | WO 2009/086361 | 7/2009 |
| WO | WO 2009/086362 | 7/2009 |
| WO | WO 2009/086363 | 7/2009 |
| WO | WO 2009/086366 | 7/2009 |
| WO | WO 2009/086367 | 7/2009 |
| WO | WO 2009/086370 | 7/2009 |
| WO | WO 2009/086372 | 7/2009 |
| WO | WO 2009/086374 | 7/2009 |
| WO | WO 2009/086377 | 7/2009 |
| WO | WO 2009/086383 | 7/2009 |
| WO | WO 2009/086407 | 7/2009 |
| WO | WO 2009/086408 | 7/2009 |
| WO | WO 2009/111330 | 9/2009 |
| WO | WO 2009/111331 | 9/2009 |
| WO | WO 2009/111332 | 9/2009 |
| WO | WO 2009/111335 | 9/2009 |
| WO | WO 2009/111342 | 9/2009 |
| WO | WO 2009/111345 | 9/2009 |
| WO | WO 2009/124017 | 10/2009 |
| WO | WO 2009/124019 | 10/2009 |
| WO | WO 2009/158576 | 12/2009 |
| WO | WO 2009/158579 | 12/2009 |
| WO | WO 2009/158580 | 12/2009 |
| WO | WO 2009/158582 | 12/2009 |
| WO | WO 2009/158583 | 12/2009 |
| WO | WO 2010/033846 | 3/2010 |
| WO | WO 2010/033848 | 3/2010 |
| WO | WO 2010/033850 | 3/2010 |
| WO | WO 2010/033852 | 3/2010 |
| WO | WO 2010/048493 | 4/2010 |
| WO | WO 2010/078297 | 7/2010 |
| WO | WO 2010/078298 | 7/2010 |

OTHER PUBLICATIONS

Coal Conversion Processes (Gasification), Encyclopedia of Chemical Technology, $4^{th}$ Edition, vol. 6, pp. 541-566.

Tandon, D., "Low Temperature and Elevated Pressure Steam Gasification of Illinois Coal", College of Engineering in the Graduate School, Southern Illinois University at Carbondale, Jun. 1996.

Ruan Xiang-Quan, et al., "Effects of catalysis on gasification of Datong coal char", FUEL, vol. 66, Apr. 1987, pp. 568-571.

Pereira, P., et al., "Catalytic Steam Gasification of Coals", Energy & Fuels, vol. 6, No. 4, 1992, pp. 407-410.

Ohtsuka, Yasuo et al., "Iron-Catalyzed Gasification of Brown Coal at Low Temperatures", Energy & Fuels, vol. 1, No. 1, 1987, pp. 32-36.

Ohtsuka, Y. et al., "Highly active catalysts from inexpensive raw materials for coal gasification", Catalysis Today, vol. 39, 1997, pp. 111-125.

Ohtsuka, Yasuo et al., "Ion-Exchanged Calcium from Calcium Carbonate and Low-Rank Coals: High Catalytic Activity in Steam Gasification", Energy & Fuels, vol. 10, No. 2, 1996, pp. 431-435.

Ohtsuka, Yasuo et al., "Steam Gasification of Coals with Calcium Hydroxide", Energy & Fuels, vol. 9, No. 6, 1995, pp. 1038-1042.

Asami, K., et al., "Highly Active Iron Catalysts from Ferric Chloride for the Steam Gasification of Brown Coal", Ind. Eng. Chem. Res., vol. 32, No. 8, 1993, pp. 1631-1636.

Ohtsuka, Yasuo et al., "Steam Gasification of Low-Rank Coals with a Chlorine-Free Iron Catalyst from Ferric Chloride", Ind. Eng. Chem. Res., vol. 30, No. 8, 1991, pp. 1921-1926.

Ohtsuka, Yasuo et al., "Calcium catalysed steam gasification of Yallourn brown coal", FUEL, vol. 65, 1986, pp. 1653-1657.

Cohen, S.J., Project Manager, "Large Pilot Plant Alternatives for Scaleup of the Catalytic Coal Gasification Process", FE-2480-20, U.S. Dept. of Energy, Contract No. EX-76-C-01-2480, 1979.

Euker, Jr., C.A., Reitz, R.A., Program Managers, "Exxon Catalytic Coal-Gasification-Process Development Program", Exxon Research & Engineering Company, FE-2777-31, U.S. Dept. of Energy, Contract No. ET-78-C-01-2777, 1981.

Kalina, T., Nahas, N.C., Project Managers, "Exxon Catalaytic Coal Gasificatoin Process Predevelopment Program", Exxon Research & Engineering Company, FE-2369-24, U.S. Dept. of Energy, Contract No. E(49-18)-2369, 1978.

Berger, R. et al., "High Temperature $CO_2$-Absorption: A Process Offering New Prospects in Fuel Chemistry", The Fifth International Symposium on Coal Combustion, Nov. 2003, Nanjing, China, pp. 547-549.

Nahas, N.C., "Exxon catalytic coal gasification process—Fundamentals to flowsheets", FUEL, vol. 62, No. 2, 1983, pp. 239-241.

Brown et al., "Biomass-Derived Hydrogen From a Thermally Ballasted Gasifier", p. 21, May 21, 2003.

Brown et al., "Biomass-Derived Hydrogen From a Thermally Ballasted Gasifier", Aug. 2005.

PCT International Search Report for International Application No. PCT/US06/24050, dated Apr. 23, 2007.

PCT International Search Report for International Application No. PCT/US06/39431, dated Mar. 28, 2007.

U.S. Appl. No. 12/778,538, filed May 12, 2010, Robinson, et al.
U.S. Appl. No. 12/778,548, filed May 12, 2010, Robinson, et al.
U.S. Appl. No. 12/778,552, filed May 12, 2010, Robinson, et al.

Adsorption, http://en.wikipedia.org/wiki/Adsorption, pp. 1-8.

Amine gas treating, http://en.wikipedia.org/wiki/Acid_gas_removal, pp. 1-4.

Coal, http://en.wikipedia.org/wiki/Coal_gasification, pp. 1-8.

Coal Data: A Reference, Energy Information Administration, Office of Coal, Nuclear, Electric, and Alternate Fuels U.S. Department of Energy, DOE/EIA-0064(93), Feb. 1995.

Deepak Tandon, Dissertation Approval, "Low Temperature and Elevated Pressure Steam Gasification of Illinois Coal", Jun. 13, 1996.

Demibras, "Demineralization of Agricultural Residues by Water Leaching", *Energy Sources*, vol. 25, pp. 679-687, (2003).

Fluidized Bed Gasifiers, http://www.energyproducts.com/fluidized_bed_gasifiers.htm, pp. 1-5.

Gas separation, http://en.wikipedia.org/wiki/Gas_separation, pp. 1-2.

Gasification, http://en.wikipedia.org/wiki/Gasification, pp. 1-6.

Gallagher Jr., et al., "Catalytic Coal Gasification for SNG Manufacture", *Energy Research*, vol. 4, pp. 137-147, (1980).

Heinemann, et al., "Fundamental and Exploratory Studies of Catalytic Steam Gasification of Carbonaceous Materials", Final Report Fiscal Years 1985-1994.

Jensen, et al. Removal of K and Cl by leaching of straw char', *Biomass and Bioenergy*, vol. 20, pp. 447-457, (2001).

Mengjie, et al., "A potential renewable energy resource development and utilization of biomass energy", http://www.fao.org.docrep/T4470E/t4470e0n.htm, pp. 1-8.

Meyers, et al. Fly Ash as A Construction Material for Highways, A Manual. Federal Highway Administration, Report No. FHWA-IP-76-16, Washington, DC, 1976.

Moulton, Lyle K. "Bottom Ash and Boiler Slag", *Proceedings of the Third International Ash Utilization Symposium*, U.S. Bureau of Mines, Information Circular No. 8640, Washington, DC, 1973.

Natural gas processing, http://en.wikipedia.org/wiki/Natural_gas_processing, pp. 1-4.

Natural Gas Processing: The Crucial Link Between Natural Gas Production and Its Transportation to Market. Energy Information Administration, Office of Oil and Gas; pp. 1-11, (2006).

Prins, et al., "Exergetic optimisation of a production process of Fischer-Tropsch fuels from biomass", *Fuel Processing Technology*, vol. 86, pp. 375-389, (2004).

Reboiler, http://en.wikipedia.org/wiki/Reboiler, pp. 1-4.

What is XPS?, http://www.nuance.northwestern.edu/KeckII/xps1.asp, pp. 1-2.

2.3 Types of gasifiers, http://www.fao.org/docrep/t0512e/T0512e0a.htm, pp. 1-6.

2.4 Gasification fuels, http://www.fao.org/docrep/t0512e/T0512e0b.htm#TopofPage, pp. 1-8.

2.5 Design of downdraught gasifiers, http://www.fao.org/docrep/t0512e/T0512e0c.htm#TopOfPage, pp. 1-8.

2.6 Gas cleaning and cooling, http://www.fao.org/docrep/t0512e0d.htm#TopOFPage, pp. 1-3.

\* cited by examiner

Slurry Drying and Steam Generation Zone 100

CATALYTIC STEAM GASIFICATION OF PETROLEUM COKE TO METHANE

FIELD OF THE INVENTION

The present invention relates to a process for converting petroleum coke to an energy source suitable for immediate use or for transport. More particularly, the present invention relates to a process for converting petroleum coke to combustible gases, such as methane.

Even more particularly, the present invention relates to a process for converting petroleum coke to pipeline quality methane, wherein process flow streams to and from the reactor are advantageously used to maximize the yield from the petroleum coke feed without undue production of waste streams and loss of catalyst.

BACKGROUND

It has long been a concern that known petroleum reserves are being rapidly consumed and exploration for new reserves is becoming more and more difficult, resulting in the prospect of a serious decline in the availability of crude oil. Unfortunately this decline is expected to coincide with mushrooming demand for energy worldwide. Thus, there is a need to develop additional energy sources, particularly in forms compatible with current technologies that rely on petroleum based fuels. One suggestion has been to convert coal to forms that can be more readily transported in pipelines, perhaps even in existing pipelines. Thus, it has been suggested to slurry coal with water or oil so that it can be transported by pipeline. However, numerous difficulties are encountered in attempting to transport coal in this manner. For example, it has proven difficult to keep the coal in suspension as a uniform mixture without undue settling. Moreover, even if such difficulties are overcome, it would be highly desirable to develop additional sources of energy that can be readily transported by tanker truck or pipeline. It would also be highly desirable to improve the efficiency of current crude oil processes so that more energy value can be secured from a given barrel of crude.

In a petroleum refinery, crude oil is converted to a product slate including gasoline, heating oil, and petrochemical feedstocks. The initial step is to distill the crude at atmospheric pressure to separate and remove light fractions. The non-vaporized fraction is subjected to vacuum distillation. These distillation processes attempt to obtain a maximum yield of liquid and gaseous hydrocarbon products from the original crude. Further liquid and vapor can be extracted from the heavy fraction that remains after vacuum distillation by subjecting such material to thermal decomposition usually in reactors called cokers, wherein the heaviest fraction of the original crude oil is converted to a solid product, conventionally called petroleum coke.

Petroleum coke is not a highly valued refinery product. It has found only a few uses, e.g., the manufacture of electrodes. Moreover, since it is a solid it is difficult to transport out of the refinery. In addition, unlike other carbon based solid materials, petroleum coke contains very little volatile material, making it difficult to burn. As such, petroleum coke is not a good fuel for combustion in ongoing refinery operations that require heat.

Accordingly, a process for converting low valued petroleum coke into a more usable energy source would be highly desirable. It would be even more desirable to convert petroleum coke into an energy source which is freely transportable in existing infrastructure such as pipelines. Moreover, as the industry turns to refining heavier and heavier crude oils, this need to convert petroleum coke to a more useful and convenient energy source will become even more apparent.

One suggestion for treating solid carbonaceous materials such as coal or petroleum coke is to convert the solids into a gaseous stream such as methane. In the 1970s, a process for converting coal into methane was suggested in U.S. Pat. No. 4,094,650 to Koh et al. The patentees therein suggested that the process could be applied to other carbonaceous sources such as petroleum coke. However, no details with respect to the application of the process to petroleum coke were provided. One skilled in the art would understand that there are significant difficulties in converting a process utilizing coal as the feed source into one utilizing petroleum coke. For example, the first step in utilizing either coal or coke is to crush the feed into appropriately sized particles. This process invariably generates large quantities of fines which are solid particles smaller than 325 mesh on the U.S. Standard Sieve Scale. As indicated above, coal fines can be used as a fuel source in conventional burners, so coal fines do not represent an undue burden in refinery operations. However, petroleum coke fines contain so little volatile matter that they are not suitable for combustion in typical burners.

One skilled would also understand that flow schemes for utilizing coal as a feed source must be vastly different than where petroleum coke is the feed rather than coal because of the different compositions of these materials. For example, coal contains a high quantity of mineral matter which must be treated differently than relatively pure carbonaceous materials.

Toward this end, it will be seen that the Koh process adds 10-20% alkali metal compound to the feed coal, and utilizes a complicated catalyst recovery system to separate the mineral matter and recycle catalyst withdrawn as part of the solid purge. Nearly one third of the withdrawn catalyst therein is irretrievably bound to the mineral matter and is lost. Large quantities of sour water, generated in the course of the process, are directed to a sour water treatment facility without further utilization in the process flow scheme.

U.S. Pat. No. 4,284,416 to Nahas discloses a process for converting coal to methane wherein a slurry of coal particles and aqueous alkali metal catalyst is dried in a fluidized bed using superheated steam to convert most of the slurry water to steam and wherein the net steam from the slurry drier is used in gasification. This process employs the sour water condensed from unreacted steam in the feed slurry water. However, a catalyst recovery process is required to leach catalyst from the solids purge and recycle to the feed mixing tank. The sour water is not used to transport catalyst back to the feed. It would be required that the feed slurry water contain sufficient dissolved alkali metal compound to deposit 10-20% of the alkali metal compound on the coal as taught by Koh et al. There is also no mention therein with respect to a consideration of the fines generated during the initial crushing of the solid feed.

U.S. Pat. No. 6,955,695 to Nahas discloses an improved catalytic gasification reactor system for the gasification of petroleum residua to methane. Petroleum residue is defined as any feedstock containing more than 50% residue which does not vaporize below an atmospheric pressure equivalent temperature of 1050° F. The reactor system employs an upper/lower two-stage process, wherein solids from a lower fluidized bed of solid particulate catalyst are combined with fresh feed and transported to the upper stage. Particles within the upper stage containing carbon and alkali metal catalyst circulate to the lower stage, while superheated steam and recycled hydrogen and carbon monoxide are fed below the lower stage. Both stages are maintained in the fluidized state. This disclosure describes converting petroleum residua to petroleum coke within the gasification reactor, and there is no disclosure of a process that can utilize solid petroleum coke as the feed for producing a high quality methane stream. The specification discloses a preferred range of solids composition for the steady state gasifier solids, but does not disclose controlling the catalyst concentration in an aqueous slurry of petroleum coke feed as a means of maintaining the composition of gasifier solids within the preferred range. One skilled in the art would understand the considerable differences and difficulties encountered when employing a solid feed, as opposed to a liquid petroleum residue. This disclosure also lacks any mention of utilizing sour water to slurry a solid carbonaceous feed, and understandably so, since this application is not concerned with a solid feed and the problems incident thereto.

Thus, it is an object of the present invention to provide a process for converting petroleum coke to a high grade energy stream.

It is also an object of the present invention to provide a process for converting petroleum coke into a form suitable for transport within a currently existing network.

Another object of the present invention is to provide a process for converting petroleum coke to a high grade methane stream suitable for shipment in a pipeline network, or in tanker trucks, to be readily distributed at terminals and the like.

A further object of the present invention is to provide an efficient catalyzed gasification process for converting petroleum coke to methane, without the need for a complicated system for catalyst recovery. The process/system disclosed herein provides integrated product purification and catalyst recycle and employs the use of spent solids to displace ammonia from sour water, minimizing the waste treatment required. The efficient process allows for nearly 100% carbon conversion to produce pipeline quality methane.

These and other objects of the invention will become apparent from the following summary and description of the invention.

SUMMARY OF THE INVENTION

The present invention provides a process for converting petroleum coke to methane wherein petroleum coke and catalyst having steam gasification activity are introduced into a slurry drying and steam generation zone to form a feed slurry. The feed slurry is introduced into a slurry drier wherein it is admixed with a stream of superheated steam to produce additional steam from the slurry water and a substantially dry solid mixture of petroleum coke impregnated with catalyst. The dried solid mixture and the net produced steam are introduced into a gasification zone where the dried solid mixture is admixed with streams of steam, $H_2$, and CO at elevated temperature and pressure to produce a raw product stream comprised of $CH_4$, $H_2S$, $CO_2$, CO, $H_2$, and $H_2O$. In another embodiment, the petroleum coke and catalyst are introduced directly into the gasification zone.

A purge of solids is withdrawn from the gasification zone in an amount sufficient to maintain a steady state load of solid inorganic compounds within the gasification zone. The unreacted steam and entrained solids are removed from the raw product stream to produce sour water and a cooled raw product stream. The solid purge comprised of catalyst and other solids is combined with the sour water to dissolve the catalyst and form a dilute aqueous catalyst solution, and to liberate ammonia from the sour water. Solids are separated from the dilute aqueous catalyst solution. The dilute aqueous catalyst solution is stripped with cooled raw product gas, and recycled to the feed slurry.

Methane is recovered from the raw product gas.

DETAILED DESCRIPTION OF THE VARIOUS EMBODIMENTS

In the process flow scheme that follows, the present invention provides an integrated process for converting petroleum coke into methane. The process efficiently utilizes fines produced during a pulverization process without undue waste. Further, sour water generated during the process is utilized to capture and recycle catalyst for additional efficiencies. Thus referring to FIG. 1, the process can include zones for feed slurry drying and steam generation, gasification, spent solids treatment, and product separation.

Figure 2:
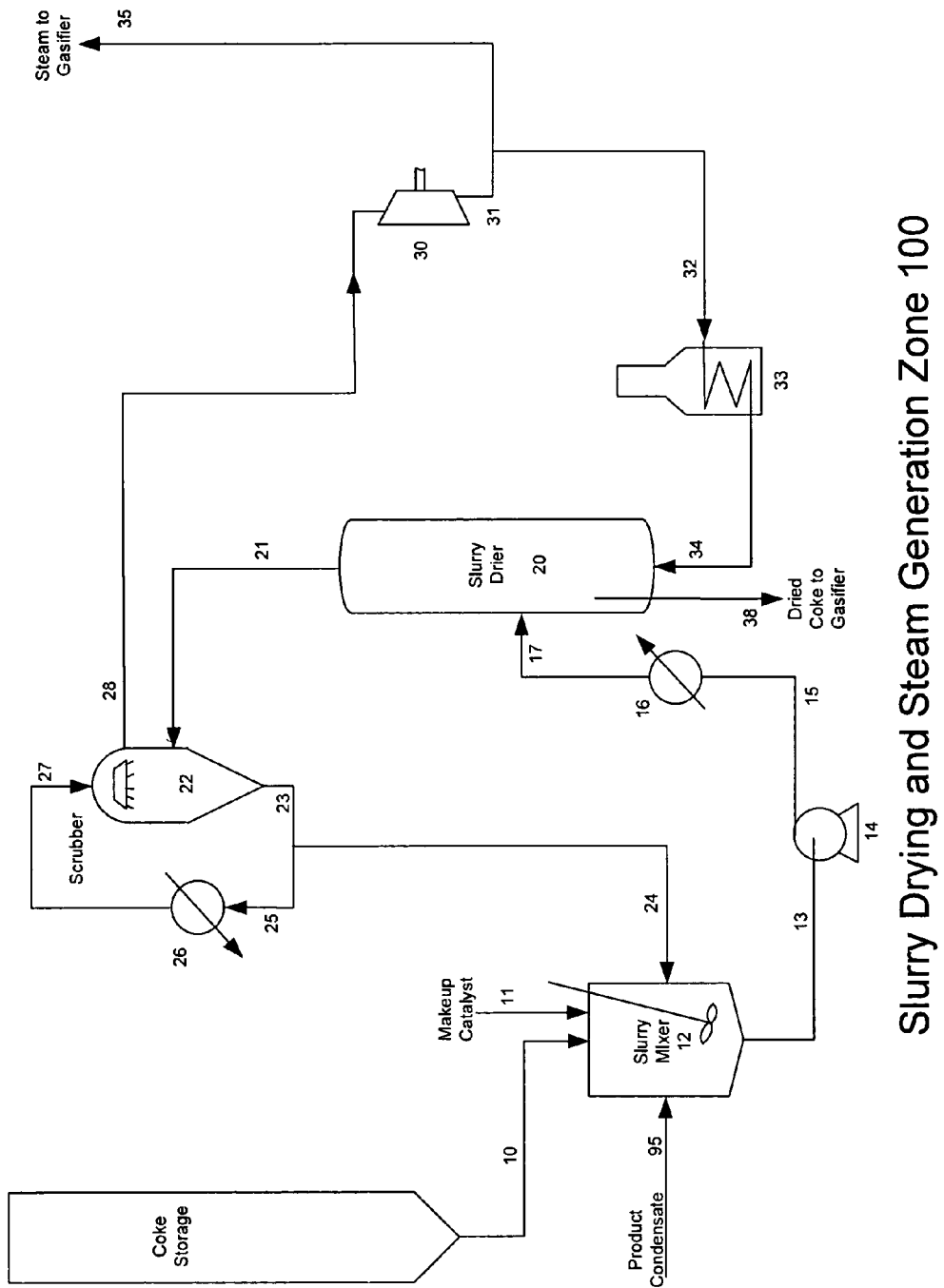
FIG. 2 is a flow diagram of a slurry drying and steam generation zone.

Petroleum coke typically has a composition of about 88.6% carbon, 2.8% hydrogen, 7.3% sulfur, 1.1% nitrogen, and 0.2% ash (percentages by mass, dry basis). Petroleum coke is typically removed from a coking reactor by a high-pressure water stream. The coke feed can contain up to 10% moisture by weight. Petroleum coke is crushed to a particle size of less than 30 mesh, and more preferably to a particle size of 30 to 100 mesh on the U.S. Standard Sieve Scale. Referring to the slurry drying and steam generation zone 100 shown in FIG. 2, the coke particles are conveyed from a storage or preparation area to a feed hopper and then through line 10 to a slurry mixing tank 12. The solid feed material can be conveyed by any of several methods. A preferred method is to pneumatically transfer the solids to the feed hopper and to the slurry-mixing tank by inert carrier gas.

Solid fines produced during the pulverization or crushing and conveying processes are recovered from the pneumatic transfer medium by scrubbing with slurry water by conventional equipment. By scrubbing the fines with feed slurry water and directing the mixture to the feed slurry-drying zone, the fines can be agglomerated into particles large enough to be gasified in the gasification zone. This enables a higher overall yield of solid carbon to gasification products than other gasification processes.

The coke particles conveyed via line 10 and any recovered fines are fed into slurry mix tank 12 where they are impregnated with a catalyst having steam gasification activity. A suitable catalyst can comprise alkali metals, alkali metal compounds, or mixtures thereof. Suitable alkali metal compounds include alkali metal: carbonates, bicarbonates, formates, oxalates, amides, hydroxides, acetates, sulfides, or similar compounds. The catalyst preferably comprises one or more of $Na_2CO_3$, $K_2CO_3$, $Rb_2CO_3$, $Li_2CO_3$, $Cs_2CO_3$, NaOH, KOH, RbOH or CsOH, and more preferably comprises potassium carbonate or potassium hydroxide. Tank 12 operates at temperatures in the range of 100° F. to 180° F. and atmospheric pressure. Catalyst can be introduced to tank 12 from several sources. Advantageously, according to one aspect of the present invention, the product condensate from separator 101 in the spent solids treatment zone 300 which is comprised of a dilute aqueous catalyst solution is introduced to slurry mixing tank 12 via line 95 at a temperature of about 150° F. In this manner, the product condensate, containing appreciable quantities of acids (often referred to as sour water) is utilized in the process, thereby avoiding or minimizing the need for expensive waste treatment operations.

Catalyst can also be introduced to tank 12 through line 24, which conveys aqueous slurry comprising substantially all of the solids entrained in the steam leaving slurry drier 20. Finally, make up catalyst can be added through line 11, as necessary, to raise the catalyst concentration to the desired level within slurry mixing tank 12. In steady state operation, the desired catalyst concentration is between 0.5 and 1.5% by mass. In determining the amount of catalyst used herein, the amounts and ratios are based on the amount of alkali in the catalyst and the amount of ash in the petroleum coke.

The solids content in the feed slurry tank 12 is between 25 and 35 wt %, preferably about 33 wt %. The concentration of potassium carbonate in slurry-mixing tank 12 is preferably such that after being dried in slurry drier 20, the potassium deposited on and within the solid particles is between 3 and 10 times more than the ash content of the coke, preferably about 5 times more than the ash content of the coke on a mass basis. It is desired to achieve approximately a 5:1 mass ratio of potassium to ash in the coke feed. With the referenced coke composition, the potassium carbonate concentration in the slurry water is about 0.9% $K_2CO_3$, allowing for moisture in the as-received coke.

The process of the invention is normally run in steady state fashion. However, it will be understood that different requirements exist for the initial startup of the process. For example, in the initial startup a higher potassium loading on the coke particles is desired, and for a coke ash content of about 0.2%, the potassium content in the slurry water can be increased to about 20% by weight, which is achieved by adjusting the potassium carbonate concentration in the slurry water to about 10% $K_2CO_3$.

Make up water, as necessary to dilute the solids concentration, can be added to the slurry mixing tank 12 directly, or can be added in combination with any stream entering tank 12.

The aqueous feed slurry of carbonaceous solids formed in slurry tank 12 is withdrawn through line 13 and passed to slurry pump 14 or similar device which raises the pressure sufficiently to enable the solids to pass through the slurry drying and steam generation zone 100 and through the gasification zone 200. This pressure is normally about 520 psig. The high-pressure slurry is then passed through heat exchanger 16 or similar device wherein the slurry temperature is raised to near the boiling point of the aqueous portion of the slurry, normally about 480° F. The preheated and pressurized feed slurry withdrawn from heat exchanger 16 is passed through line 17 into fluid bed slurry dryer 20 or similar device.

Slurry dryer 20 contains a fluidized bed of carbonaceous solids extending upward within the vessel above an internal grid or similar distribution device. The bed is maintained in a fluidized state by means of superheated steam introduced into the bottom of the dryer through bottom inlet line 34. The pressure in the fluid bed slurry dryer 20 is normally maintained in a range between the pressure maintained in the gasification reactor 55, and about 200 psi above the gasification reactor pressure. The temperature of the steam exiting dryer 20 will normally range between the saturation temperature of steam at the operating pressure in the dryer and about 200° F. above the saturation temperature at the dryer operating pressure. For a unit having a feed rate of 2500 tons per day of coke and a solids residence time in the fluidized bed dryer of about 20 minutes, the bed holdup can be about 30 tons, i.e., about 2000 ft³ at a density of 35 lb/ft³. It is normally desired to achieve a superficial velocity of about 2 ft/sec. At such conditions, the slurry dryer bed diameter can be about 14.2 ft and the bed depth can be about 12.6 ft.

Within the fluidized bed of the slurry dryer 20, the aqueous feed slurry is contacted with superheated steam injected into the dryer through line 34. The superheated steam is injected into the dryer at about 1100° F. The sensible heat in the superheated steam can vaporize substantially all of the water in the aqueous feed slurry thereby converting it into steam. At these conditions, about one pound of water in the slurry feed can be vaporized to steam using about two pounds of the superheated steam injected to slurry drier 20 from line 34. Dryer 20 is normally operated so that the dry carbonaceous solids contain between about 0.1 and about 4.0 weight percent water.

The gas leaving the fluidized bed in slurry dryer 20 is comprised primarily of steam. The slurry drier can include one or more cyclone separators or the like above the fluidized bed for removing relatively large particles from the steam.

The steam withdrawn overhead from slurry dryer 20 through line 21 can be directed through a wet scrubber 22 or similar device where it is contacted with scrubber water introduced through line 27. A portion of the scrubber water is cooled and recirculated to the top of the scrubber, where it cools the steam from about 480° F. to about 450° F. Enough steam is condensed to carry the scrubbed fines in a slurry to the feed slurry mixing tank 12 through line 24.

The scrubbed steam is withdrawn from the wet scrubber 22 through line 28 and passed to compressor 30 where its pressure is increased to about 560 psig. Pressurized steam is withdrawn from compressor 30 through line 31. The net steam, at a mass flow equal to the mass flow of vaporized slurry water, is directed to gasification zone 200 through line 35. The remaining steam, which can be considered to act as a heat transfer medium, is passed through line 32 to superheater 33 or similar furnace where the steam is superheated to a temperature of about 1100° F. The superheated steam exiting superheater 33 is passed through line 34 into slurry dryer 20 where its sensible heat serves to convert the water in the feed slurry (including the water in the coke pores) into steam while simultaneously heating the feed particles, catalyst and unconverted water to an elevated temperature.

Figure 1:
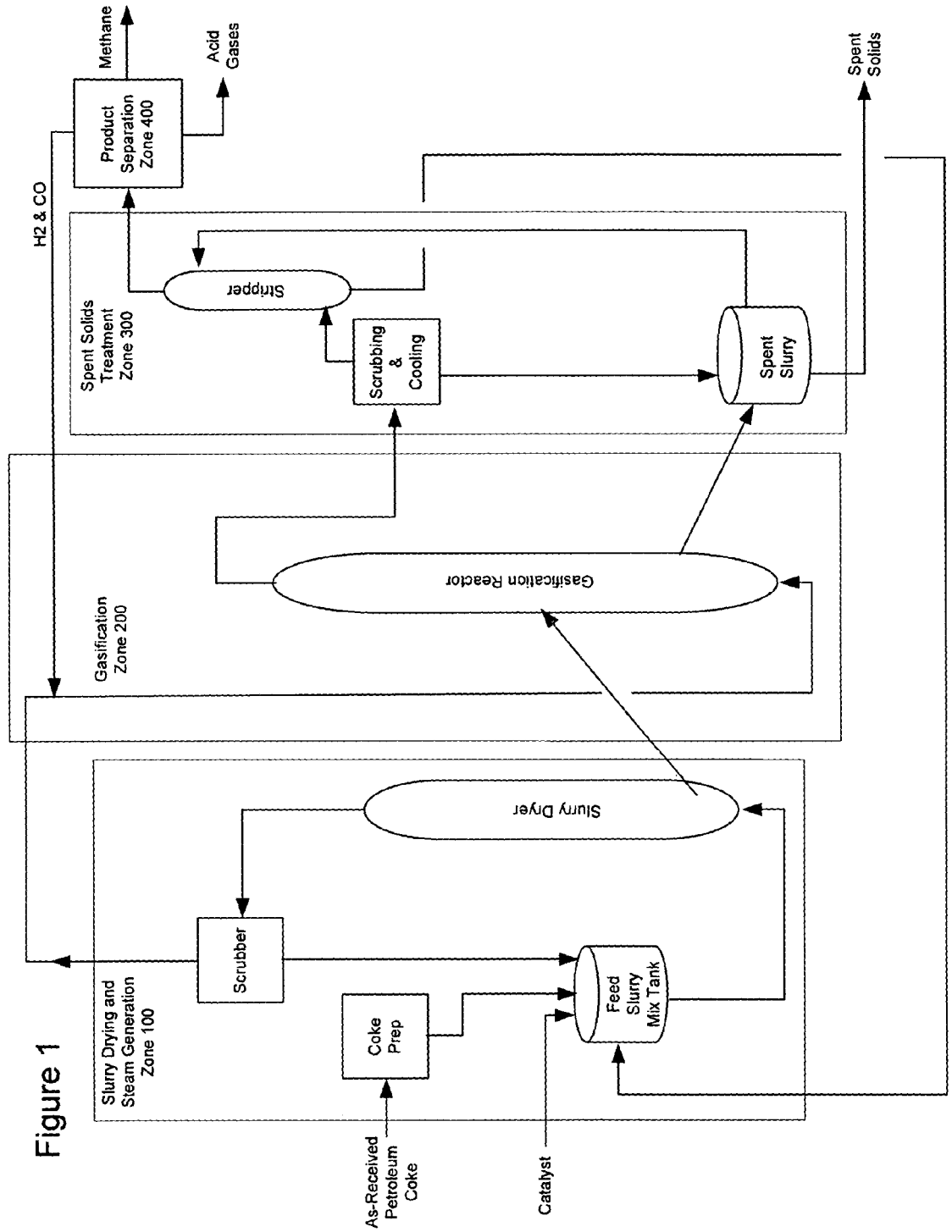
FIG. 1 is a schematic diagram of the zones that can be utilized in the processes of the invention in which Zone 100 represents the slurry system depicted in FIG. 2, Zone 200 represents the gasification system depicted in FIG. 3, Zone 300 represents the spent solids treatment depicted in FIG. 4, and Zone 400 represents conventional gas processing not otherwise shown.
Figure 3:
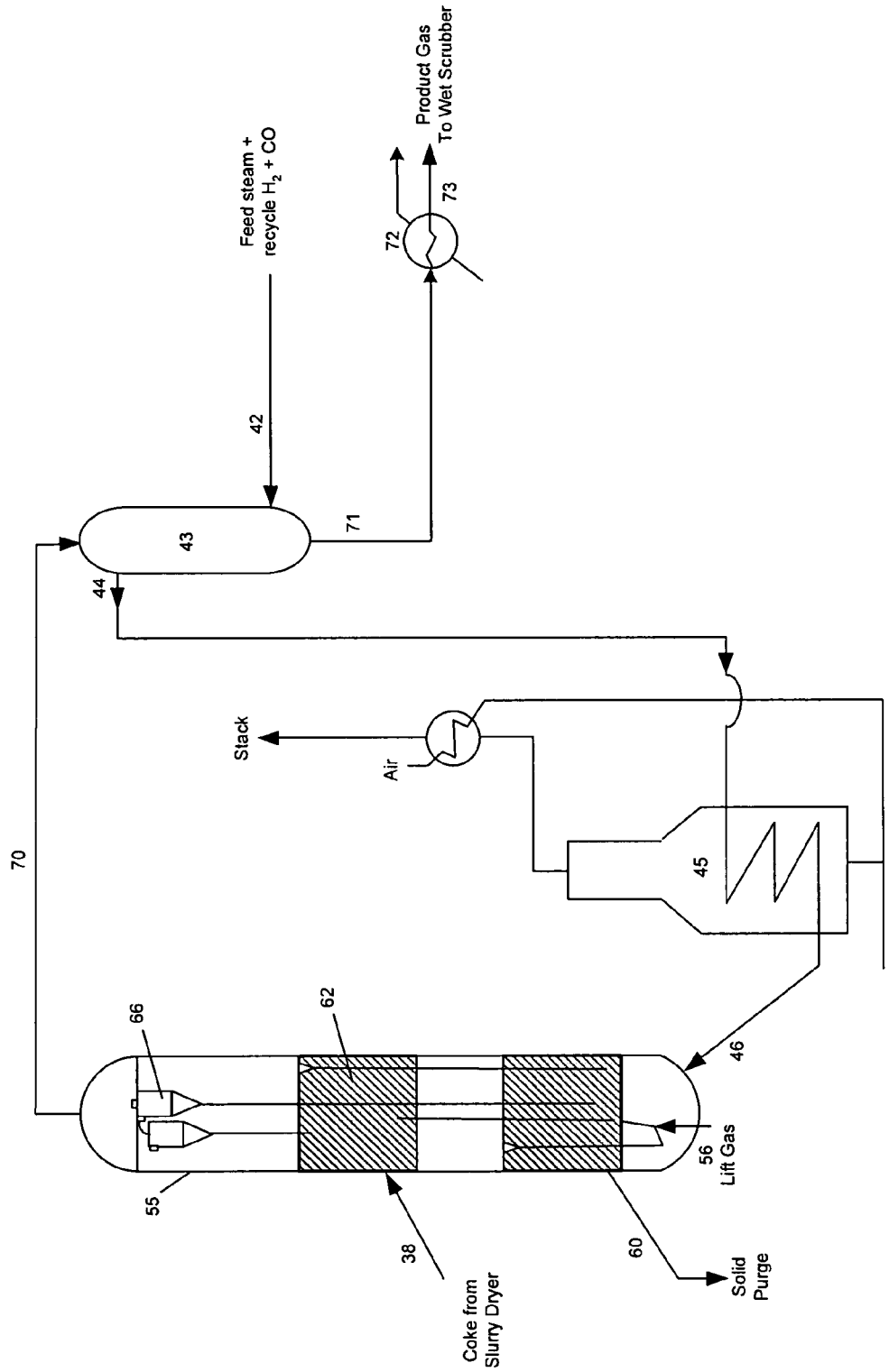
FIG. 3 is a flow diagram of a gasification zone.

As shown in FIG. 1, the net steam passes from zone 100 into gasification zone 200 where it is combined with $H_2$ and CO. Preferably, the $H_2$ and CO are obtained by recycling the hydrogen and carbon monoxide recovered from the raw product gas emanating from the gasification zone discussed hereafter. Generally these components are separated from the product gases by cryogenic distillation techniques which are well known in the art. Referring now to FIG. 3, the net steam, $H_2$ and CO mixture in line 42 is passed to heat exchanger 43 where it is heated to about 1150° F. by indirect heat exchange with the hot raw product gas from gasification reactor 55, which is introduced into the exchanger at about 1300° F. through line 70. The heated steam mixture is passed through line 44 to preheat furnace 45 or similar device where it is further superheated to superheater outlet temperature of about 1450° F. prior to its injection into gasification reactor 55. The preheated steam is withdrawn from furnace 45 and passed through line 46 into gasification reactor 55. The actual temperature of the superheater outlet is controlled to maintain the gasification reactor at the desired temperature, in this example at 1300° F.

Dryer 20 can be operated such that substantially all of the steam required in gasification reactor 55 is provided through line 35 and no makeup steam from any other source will be required. The dried carbonaceous solids produced in fluid bed slurry dryer 20 are withdrawn from the dryer through line 38, passing from zone 100 into the gasification zone 200.

In gasification zone 200, any of several gasification reactors can be utilized in the process of the invention. One such preferred reactor is a two stage fluidized bed reactor of the type disclosed in U.S. Pat. No. 6,955,695 to Nahas. However, gasification reactor 55 need not be operated with two stages, and indeed, need not utilize a fluidized bed. The pressure in gasification reactor 55 will normally be about 500 psig. The gasification reactor temperature will normally be maintained between about 1000° F. and about 1500° F., preferably between about 1200° F. and about 1400° F. The lift gas utilized in gasification reactor 55 is normally a portion of the superheated mixture introduced in line 46. The solids in line 38 are injected into upper fluidized bed 62 within gasification reactor 55. Slurry dryer 20 is operated at a pressure that is normally above the operating pressure of gasification reactor 55. Hence, the solids can be directly passed into the gasification reactor 55 without further pressurization. Thus, complicated systems for pressurizing dry solids, such as lock-hoppers, are not required. However, according to the present invention, it is contemplated that dry solids may also be utilized in the process of the invention without the need for the slurry drying operation of zone 100. If that is desired, the dry petroleum coke feed stream can be introduced directly into the gasification reactor using appropriate lock hoppers or similar mechanisms as required. According to this embodiment, the catalyst can be introduced as dry solid mixed with the coke or impregnated on the coke or fed separately as a dry solid.

Referring again to the gasification zone 200 shown in FIG. 3, under the conditions in gasification reactor 55, the steam mixture reacts with and converts about 97% of the coke into a gaseous product composed primarily of methane and carbon dioxide. Hydrogen and carbon monoxide are present in the product gas at equilibrium, but are separated and recycled such that there is no net production of these gas components. Sulfur in the feed reacts with hydrogen and carbon monoxide to form hydrogen sulfide and trace concentrations of carbonyl sulfide. Nitrogen in the feed reacts quantitatively with hydrogen to form ammonia. Internal cyclone separators 66 remove the larger solids entrained in the hot raw product and return them to gasification reactor 55.

A minimum possible solid purge 60 is desirable, but should be sufficient to remove the ash or mineral matter in the fresh feed. In a unit processing 2500 tons per day fresh petroleum coke containing about 0.2% ash, the solid purge 60 together with the overhead fines can total about 60 tons per day. Methods of withdrawing solids from the reactor for sampling or purging are well known to those skilled in the art. One such method taught by EP0102828 (1984), for example, can be employed.

The hot raw product gas includes about 32% unreacted steam and entrained fines which escape the internal cyclones 66. The gasification reactor raw product is withdrawn from gasification reactor 55 through line 70 at about 1300° F. and cooled in exchanger 43 to about 815° F. The raw product leaving heat exchanger 43 in line 71 is further cooled in waste heat boiler 72 or similar device to about 400° F. The temperature of the gas leaving heat exchanger 72 in line 73 is controlled to be above the dew point to keep the entrained fines dry until they reach fines scrubber 74.

Figure 4:
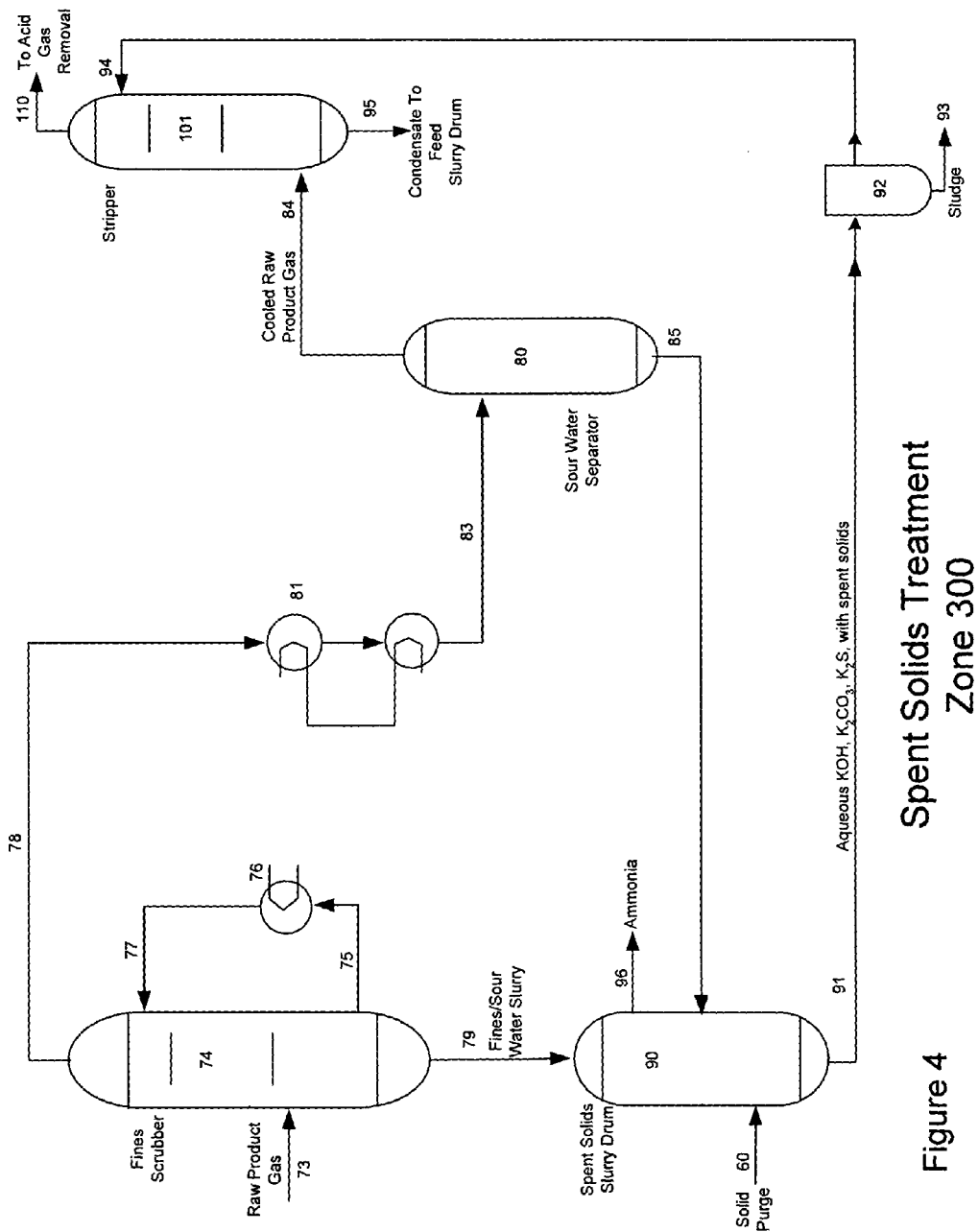
FIG. 4 is a flow diagram of a spent solids treatment zone.

Referring now to FIG. 4, the raw product gas in line 73 flows through fines scrubber 74 wherein the entrained fines are removed and the raw product is further cooled to 350° F. by the scrubber water. The scrubber water is pumped from the lower portion of scrubber 74 through line 75 to scrubber cooler 76 and then circulated to the top of the scrubber 74 through line 77. At these conditions, about 10% of the unreacted steam condenses and, together with the removed fines, forms a fines and sour water slurry which is directed to spent solids slurry drum 90 through line 79.

The raw product passes through line 78 and is further cooled in boiler feed water preheaters 81 or similar devices to about 100° F. which condenses almost all of the remaining unreacted steam. The raw product passes through sour water separator 80 wherein the condensate forms a second sour water stream and is directed to the spent solids slurry drum 90 through line 85. The cooled raw product now containing only about 0.2% unreacted steam is directed through line 84 into raw product stripper 101.

The sour water drained from sour water separator 80 through line 85 is combined with the fines and sour water slurry drained from the fines scrubber through line 79 and mixed with solid purge 60 in spent solids slurry drum 90. The solids mixture has a steady state composition of about 58% coke, 35% potassium and 7% other inorganics, mainly nickel and vanadium. Most of the potassium is solubilized as potassium hydroxide with some potassium sulfide. The alkalinity of the resulting slurry at a temperature of about 100° F. drives out ammonia from the sour water condensate, and the ammonia is recovered overhead from the spent solids slurry drum 90 through line 96.

The spent solids slurry from spent solids slurry drum 90 containing about 2.4% solids in aqueous solution of KOH, $K_2S$, and $K_2CO_3$ drains through line 91 to separator 92. For a unit processing about 2500 tons per day fresh petroleum coke containing about 0.2% ash, about 40 tons per day solids purge in the sludge can be withdrawn through line 93. The aqueous solution withdrawn from separator 92 through line 94 is contacted with cooled raw product gas in raw product stripper 101 wherein the aqueous $K_2S$ and KOH are converted to aqueous $K_2CO_3$ and gaseous $H_2S$. The conversion of the aqueous catalyst to the carbonate form can be achieved by contacting with other gas streams containing $CO_2$. The dilute aqueous catalyst solution of $K_2CO_3$ is recycled to the feed slurry mixer 12 through line 95. The cooled raw product gas together with $H_2S$ formed in stripper 101 is directed downstream through line 110 to product separation zone 400 for acid gas removal and separation of $H_2$ and CO from the product $CH_4$ by conventional means. Methane can be recovered by cryogenic distillation with a purity of more than 99.9% and be suitable for direct shipment in natural gas pipelines or for recovery as liquid methane for delivery to liquefied natural gas terminals.

As will be seen from the above, the invention disclosed herein provides a process for converting low valued petroleum coke into methane which is freely transportable in existing infrastructure such as pipelines.

By utilizing the coke fines generated in the process and converting them into methane, the present process provides a higher conversion of carbon to methane for a given carbon content of the solid starting material. The coke catalytic gasification process of the invention also provides an efficient catalyzed gasification process for conversion of petroleum coke to methane, without the need for a complicated system for catalyst recovery and accompanying process problems. The process/system provides integrated product purification and catalyst recycle minimizing the waste treatment required.

The present invention also recaptures the sour water condensed from the raw product stream. Such utilization maintains the sour water within the process and eliminates or substantially reduces the need for sour water waste treatment. The sour water is advantageously utilized to dissolve the catalyst in the solid purge and recycle the catalyst to the feed. The recycled catalyst solution is dilute, which allows for less expensive materials of construction.

The present invention can be operated such that essentially all the sulfur of the feed is contained in the raw product gases and therefore can be removed primarily in a single gaseous treatment unit. Essentially all of the ammonia produced from any nitrogen in the feed can be recovered overhead from the spent solids slurry tank.

The invention has been described in conjunction with a particular flow diagram and operating conditions, various modifications and substitutions can be made thereto without departing from the spirit and scope of the present invention. No limitation should be imposed other than those indicated by the following claims.

The invention claimed is:

1. A process for converting petroleum coke to methane, comprising
    combining petroleum coke and a catalyst having steam gasification activity in an aqueous medium to form a feed slurry;
    introducing said feed slurry and superheated steam into a slurry drier to produce net steam and substantially dry solid particles of petroleum coke impregnated with catalyst;
    reacting said dry solid particles with said net steam in a gasification reactor to form a raw product gas comprised of unreacted steam, methane, carbon dioxide, hydrogen, and carbon monoxide;
    recovering methane from said raw product gas; and
    controlling the concentration of catalyst in said aqueous medium based on the amount of ash in said petroleum coke.

2. The process of claim 1 wherein said catalyst having steam gasification activity comprises one or more from the group consisting of alkali metals and alkali metal compounds.

3. The process of claim 2 wherein said alkali metal compounds are selected from the group consisting of alkali metal carbonates, alkali metal bicarbonates, alkali metal formates, alkali metal oxalates, alkali metal amides, alkali metal hydroxides, alkali metal acetates, and alkali metal sulfides.

4. The process of claim 2 wherein said catalyst comprises one or more alkali metal compounds selected from the group consisting of $Na_2CO_3$, $K_2CO_3$, $Rb_2CO_3$, $Li_2CO_3$, $Cs_2CO_3$, NaOH, KOH, RbOH and CsOH.

5. The process of claim 2 wherein said catalyst comprises potassium carbonate or potassium hydroxide.

6. The process of claim 5 wherein said potassium carbonate concentration in said aqueous medium is in the range of about 0.9 to 10 wt %.

7. A process for converting petroleum coke to methane, comprising:
    combining petroleum coke and a catalyst having steam gasification activity in an aqueous medium to form a feed slurry;
    introducing said feed slurry and superheated steam into a slurry drier to produce net steam and substantially dry solid particles of petroleum coke impregnated with catalyst;
    reacting said dry solid particles and said net steam in a gasification reactor to form a raw product gas comprised of unreacted steam, methane, carbon dioxide, hydrogen, and carbon monoxide;
    withdrawing a solid purge from said reactor, said solid purge comprising coke material and having catalyst incorporated therewith; cooling said raw product stream to condense unreacted steam to form sour water and a stream of cooled raw product gas;
    recovering methane from said raw product gas;
    contacting said solid purge with said sour water to dissolve said incorporated catalyst to form a dilute aqueous catalyst solution, and
    returning said dilute aqueous catalyst solution to said feed slurry.

8. The process of claim 7 wherein the solid purge from the gasification reactor is contacted with said sour water in a slurry vessel, and ammonia vapor is recovered from said slurry vessel.

9. The process of claim 7 wherein said dilute catalyst solution is contacted with a gas containing $CO_2$ before returning to said feed slurry.

10. The process of claim 7 wherein said dilute catalyst solution is stripped with said cooled raw product gas before returning to said feed slurry.

11. A process for gasifying petroleum coke comprising:
    crushing petroleum coke to produce petroleum coke particles having a mesh size larger than about 325 mesh on the U.S. Standard Sieve Scale and a stream of petroleum coke fines;
    combining said petroleum coke particles and at least part of said petroleum coke fines with a catalyst having steam gasification activity in an aqueous medium to form a feed slurry;
    introducing said feed slurry and superheated steam into a slurry drier to produce net steam and substantially dry solid particles of petroleum coke impregnated with catalyst;
    reacting said dry solid particles and said net steam in a gasification reactor.

12. The process of claim 11 wherein said petroleum coke particles range in size from 33 to 100 mesh.

13. The process of claim 11 wherein said reactor comprises a fluidized bed.

14. A process for converting petroleum coke to methane, comprising:
    introducing dry petroleum coke, catalyst having steam gasification activity, and superheated steam to a gasification reactor;
    reacting said coke, catalyst, and steam to form a raw product gas comprised of unreacted steam, methane, carbon dioxide, hydrogen, and carbon monoxide;
    withdrawing a solid purge from said reactor, said solid purge comprising coke material and having catalyst incorporated therewith;
    cooling said raw product stream to condense unreacted steam to form sour water and a stream of cooled raw product gas; contacting said solid purge with said sour water in a slurry vessel;
    recovering ammonia vapor from said slurry vessel; and
    recovering methane from said raw product gas.

15. The process of claim 1 wherein said net steam is combined with $H_2$ and CO and superheated prior to said gasification reactor.

16. The process of claim 7 wherein said net steam is combined with $H_2$ and CO and superheated prior to said gasification reactor.

17. The process of claim 14 wherein said superheated steam has been combined with $H_2$ and CO and superheated prior to said gasification reactor.

18. The process of claim 1 wherein the gasification reactor is maintained at a temperature between about 1000° F. and about 1500° F.

19. The process of claim 7 wherein the gasification reactor is maintained at a temperature between about 1000° F. and about 1500° F.

20. The process of claim 14 wherein the gasification reactor is maintained at a temperature between about 1000° F. and about 1500° F.

* * * * *